United States Patent

Hámori et al.

Patent Number: 5,756,495
Date of Patent: May 26, 1998

[54] 3-SUBSTITUTED 3H-2, 3-BENZODIAZEPINE DERIVATIVES, THE PRODUCTION AND USE AS PHARMACEUTICAL AGENTS

[75] Inventors: Tamás Hámori; István Tarnawa; Sándor Sólyom; Pál Berzsenyi; Erzsébet Birkás; Ferenc Andrási; István Ling; Tibor Haskó, all of Budapest; Gábor Kapus, Dunakeszi; Emese Csuzdi, Budapest; Márta Szöllösy, Budapest; Franciska Erdö, Budapest; Antal Simay, Budapest; Gábor Zólyomi, Budapest, all of Hungary

[73] Assignee: Schering Aktiengesellschaft, Berlin, Germany

[21] Appl. No.: 776,536

[22] PCT Filed: Jul. 28, 1995

[86] PCT No.: PCT/DE95/01029

§ 371 Date: Apr. 23, 1997

§ 102(e) Date: Apr. 23, 1997

[87] PCT Pub. No.: WO96/04283

PCT Pub. Date: Feb. 15, 1996

[30] Foreign Application Priority Data

Aug. 1, 1994 [DE] Germany ................ 44 28 835.2

[51] Int. Cl.⁶ .................. A61K 31/55; C07D 491/00
[52] U.S. Cl. ........................... 514/220; 540/557
[58] Field of Search ................ 540/557; 514/220

[56] References Cited

FOREIGN PATENT DOCUMENTS 492485  7/1992  European Pat. Off. .

OTHER PUBLICATIONS

Gatta et al., Derivatives of 2,3–Benzodiazepine(*), Farmaco, Edizione Scientifica, vol. 40, No. 12, pp. 942–955, 1985.

Primary Examiner—Mukunk J. Shah
Assistant Examiner—Brenda Coleman
Attorney, Agent, or Firm—Millen, White, Zelano & Branigan, P.C.

[57] ABSTRACT

New 3-substituted 3H-2,3-benzodiazepine derivatives of general formula I

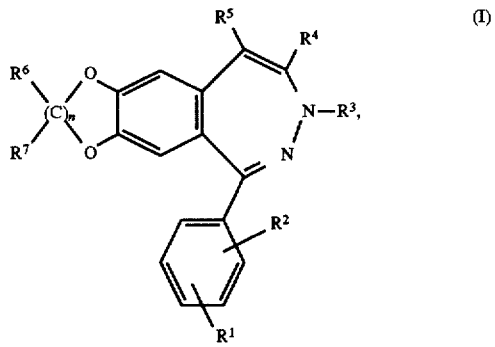

in which $R^1$, $R^2$, $R^3$, $R^4$, $R^5$, $R^6$, $R^7$ and n have the meanings indicated in the description, their production as well as their use as pharmaceutical agents are described.

8 Claims, No Drawings

3-SUBSTITUTED 3H-2, 3-BENZODIAZEPINE DERIVATIVES, THE PRODUCTION AND USE AS PHARMACEUTICAL AGENTS

This application is a 371 of PCT/DE95/01029 filed Jul. 28, 1995.

The invention relates to new 3-substituted 3H-2,3-benzodiazepine derivatives, their production and use as pharmaceutical agents.

It is already known that selected 2,3-benzodiazepine derivatives have modulatory activity at quisqualate receptors and owing to this property are suitable as pharmaceutical agents for treating diseases of the central nervous system.

It has now been found that 3-substituted 3H-2,3-benzodiazepine derivatives of general formula I

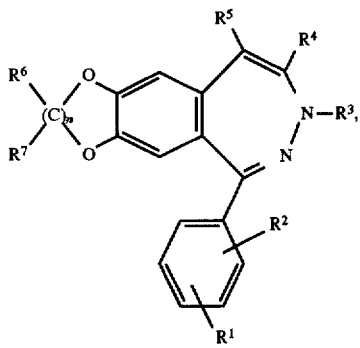

(I)

in which $R^1$ and $R^2$ are the same or different and mean hydrogen, $C_1$–$C_6$ alkyl, nitro, halogen, the group —$NR^8R^9$, —O—$C_{1-4}$ alkyl or —$CF_3$, $R^3$ means the group

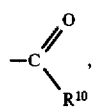

$R^4$ means optionally substituted $C_1$–$C_6$ alkyl, $R^5$ means hydrogen or optionally substituted $C_1$–$C_6$ alkyl, $R^6$ and $R^7$ are the same or different and mean hydrogen, optionally substituted $C_1$–$C_6$ alkyl or optionally substituted aryl, $R^8$ and $R^9$ are the same or different and mean hydrogen, $C_1$–$C_6$ alkyl or the group

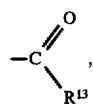

$R^{10}$ means hydrogen, optionally substituted $C_1$–$C_6$ alkyl, optionally substituted aryl, the group —$NR^{11}R^{12}$, —O—$C_{1-6}$ alkyl, $C_{3-7}$ cycloalkyl, $C_{2-6}$ alkenyl or —O—$C_{3-7}$ cycloalkyl, $R^{11}$ and $R^{12}$ are the same or different and mean hydrogen, optionally substituted $C_1$–$C_6$ alkyl or optionally substituted aryl, and $R^{13}$ means $C_1$–$C_6$ alkyl and n stands for 1, 2 or 3 as well as their isomers and physiologically compatible salts, also are suitable for treating diseases of the central nervous system, whereby the compounds are distinguished by better properties compared to the above-mentioned prior art. Since an optically active center is present neither in 4-position nor in 5-position, the compounds of formula I also are easily accessible without separation of enantiomers.

Alkyl is defined as a straight-chain or branched alkyl radical, such as, for example, methyl, ethyl, propyl, isopropyl, butyl, isobutyl, sec-butyl, pentyl, isopentyl or hexyl, which can be substituted—like the aryl radical—optionally by $C_1$–$C_6$ alkoxy, halogen or $C_1$–$C_6$ alkanoyl.

If a halogenated alkyl radical is present, the latter can be halogenated or perhalogenated in several places.

Halogen is defined as fluorine, chlorine, bromine and iodine.

The aryl radical can contain 6–10 carbon atoms, whereby phenyl is preferred.

Cycloalkyl is defined in each case as cyclopropyl, cyclobutyl, cyclopentyl, cyclohexyl and cycloheptyl, especially $C_{3-5}$ cycloalkyl.

The alkenyl radicals can be straight-chain or branched. For example, 2-propenyl, 3-methyl-2-propenyl, 2-butenyl, methallyl and vinyl can be mentioned.

Alkanoyl radicals are derivatives of aliphatic carboxylic acids, such as, for example, formic acid, acetic acid, propionic acid, butyric acid, caproic acid, valeric acid, trimethylacetic acid, i.a.

The physiologically compatible salts are derived from inorganic and organic acids. Suitable are inorganic acids, such as, for example, hydrohalic acids such as hydrochloric acid, hydrobromic acid, phosphoric acid, sulfuric acid or organic acids, such as, for example, aliphatic or aromatic mono- or dicarboxylic acids such as formic acid, acetic acid, maleic acid, fumaric acid, succinic acid, lactic acid, tartaric acid, citric acid, oxalic acid, glyoxylic acid or sulfonic acids, for example, $C_{1-4}$ alkanesulfonic acids such as methanesulfonic acid or benzenesulfonic acids that are optionally substituted by halogen or $C_{1-4}$ alkyl, such as p-toluenesulfonic acid.

The compounds of formula I also comprise the E- or Z-isomers, or, if a chiral center is present, their racemates or enantiomers.

Preferred compounds of general formula I are those in which $R^1$ means amino or nitro.

Especially preferred compounds of general formula I are those in which $R^1$ means nitro or amino, $R^2$ means hydrogen, $R^3$ means the group

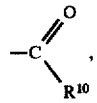

$R^4$ means methyl or ethyl, $R^5$, $R^6$ and $R^7$ mean hydrogen, $R^{10}$ means hydrogen, $C_1$–$C_6$ alkyl, phenyl optionally substituted with halogen, the group —$NR^{11}R^{12}$, $C_{3-7}$ cycloalkyl, $C_{2-6}$ alkenyl, —O—$C_{1-6}$ alkyl or $C_{1-6}$ alkyl, which is substituted in one or more places with fluorine, $R^{11}$ and $R^{12}$ are the same or different and mean hydrogen, $C_1$–$C_4$ alkyl or phenyl and n means 1, 2 or 3.

The compounds of general formula I as well as their physiologically compatible salts can be used as pharmaceutical agents owing to their non-competitive inhibition of the AMPA receptors. Owing to their profile of action, the compounds according to the invention are suitable for treating diseases that are caused by hyperactivity of excitatory amino acids, such as, for example, glutamate or aspartate. Since the new compounds act as non-competitive antagonists of excitatory amino acids, they are suitable especially for treating those diseases that are influenced by the receptors of excitatory amino acids, especially the AMPA receptor.

The pharmacological action of the compounds of formula I was determined by means of the tests described below:

Male NMRI mice weighing 18–22 g were kept under controlled conditions (0600–1800 hours light/dark cycle, with free access to food and water) and their assignment to groups was randomized. The groups consisted of 5–16 animals. The observation of the animals was performed between 0800 and 1300 hours.

AMPA was sprayed into the left ventricles of mice that were allowed to move freely. The applicator consisted of a cannula with a device made of stainless steel, which limits the depth of injection to 3.2 mm. The applicator was connected to an injection pump. The injection needle was inserted perpendicular to the surface of the skull according to the coordinates of Montemurro and Dukelow. The animals were observed up to 180 sec. until clonic or tonic seizures set in. The clonic movements, which last longer than 5 sec., were counted as seizures. The beginning of the clonic seizures was used as an endpoint for determining the seizure threshold. The dose that was necessary to raise or reduce the seizure threshold by 50% ($THRD_{50}$) was determined in 4–5 experiments. The $THRD_{50}$ and the confidence limit were determined in a regression analysis.

The results of these tests show that the compound of formula I and its acid addition salts influence functional disorders of the AMPA receptor. They are therefore suitable for the production of pharmaceutical agents for symptomatic and preventive treatment of diseases that are triggered by changing the function of the AMPA receptor complex.

The treatment with the compounds according to the invention prevents or delays the cell damage that occurs as a result of disease and functional disorders and reduces the concomitant symptoms.

According to the invention, the compounds can be used for treating neurological and psychiatric disorders that are triggered by overstimulation of the AMPA receptor. The neurological diseases, which can be treated functionally and preventatively, include, for example, neurodegenerative disorders such as Parkinson's disease, Alzheimer's disease, Huntington's chorea, amyotropic lateral sclerosis, and olivopontocerebellar degeneration. According to the invention, the compounds can be used for the prevention of postischemic cellular degeneration, cellular degeneration after brain trauma, in the case of stroke, hypoxia, anoxia and hypoglycemia and for the treatment of senile dementia, AIDS dementia, neurological symptoms that are related to HIV infections, multiinfarct dementia as well as epilepsy and muscle spasms. The psychiatric diseases include anxiety conditions, schizophrenia, migraines, pain conditions as well as the treatment of sleep disorders and withdrawal symptoms after drug abuse such as in alcohol, cocaine, benzodiazepine or opiate withdrawal. In addition, the compounds can be used in the prevention of tolerance development during long-term treatment with sedative pharmaceutical agents, such as, for example, benzodiazepines, barbiturates and morphine. Moreover, the compounds can be used as anesthetics (anesthesia), analgesics or anti-emetics.

For use of the compounds according to the invention as pharmaceutical agents, the latter are brought into the form of a pharmaceutical preparation, which in addition to the active ingredient for enteral or parenteral administration contains suitable pharmaceutical, organic or inorganic inert media, such as, for example, water, gelatin, gum arabic, lactose, starch, magnesium stearate, talc, vegetable oils, polyalkylene-glycols, etc. The pharmaceutical preparations can be present in solid form, for example, as tablets, coated tablets, suppositories, capsules or in liquid form, for example as solutions, suspensions or emulsions. Moreover, they optionally contain adjuvants such as preservatives, stabilizers, wetting agents or emulsifiers, salts for changing the osmotic pressure or buffers.

For parenteral use, especially injection solutions or suspensions, especially aqueous solutions of the active compounds in polyhydroxyethoxylated castor oil, are suitable.

As vehicle systems, surface-active adjuvants such as salts of bile acids or animal or vegetable phospholipids, but also mixtures of them as well as liposomes or their components, can also be used.

For oral use, especially tablets, coated tablets or capsules with talc and/or hydrocarbon vehicles or binders, such as, for example, lactose, corn or potato starch, are suitable. The substance may also be administered in liquid form, such as, for example, as juice, to which optionally a sweetener is added.

The dosage of the active ingredients can vary depending on method of administration, age and weight of the patient, type and severity of the disease to be treated and similar factors. The daily dose is 0.5–1000 mg, preferably 50–200 mg, whereby the dose can be given as a single dose to be administered once or divided into two or more daily doses.

The production of the compounds according to the invention is carried out according to methods that are known in the art. For example, compounds of formula I are obtained in that a compound of formula II

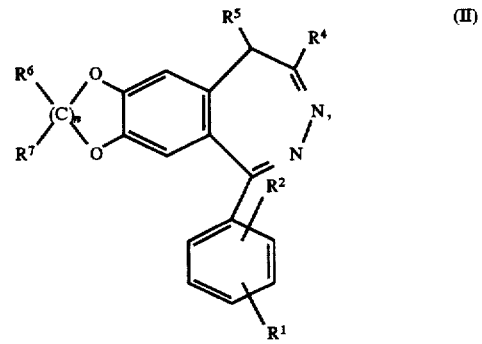

in which $R^1$, $R^2$, $R^4$, $R^5$, $R^6$, $R^7$ and n have the meanings indicated in general formula I, is acylated, and optionally the nitro group is catalytically reduced at $R^1$ and/or $R^2$ and then the carbamoyl group is optionally acylated, alkylated, halogenated with organic amines or the ester group is introduced with alcohols, the isomers are separated or the salts are formed.

The acylation can be performed with or without solvent at room temperature or a higher temperature with the commonly used acylating agents. As acylating agents, anhydrides or acid halides are suitable. As anhydrides, mixed or else symmetrical anhydrides can be used. If the acylation is performed with chloroformic acid esters such as chloroformic acid phenyl ester, the corresponding carbamoyl compounds are obtained by subsequent reaction with primary and secondary organic amines such as methylamine or the corresponding ester group can be introduced by reaction with alcohols such as methanol, ethanol optionally in the presence of catalytic amounts of NaCN.

The reduction in the nitro group is performed in polar solvents at room temperature or a higher temperature. As catalysts for reduction, metals such as Raney nickel or noble metal catalysts such as palladium or platinum optionally on vehicles are suitable. Instead of hydrogen, for example, ammonium formate or hydrazine can also be used in a known way. Reducing agents such as tin(II) chloride or titanium(III) chloride can also be used as complex metal hydrides optionally in the presence of heavy metal salts. Iron can also be used as a reducing agent. The reaction is then performed in the presence of an acid such as, e.g., acetic acid or ammonium chloride, optionally with the addition of a solvent, such as, for example, water or methanol.

If alkylation of an amino group is desired, it can be alkylated according to commonly used methods—for example with alkyl halides—or according to the Mitsonubo variant by reaction with an alcohol in the presence of triphenylphosphine and azodicarboxylic acid ester, or the amine can be subjected to reductive amination with aldehydes or ketones optionally in succession with two different carbonyl compounds, whereby mixed derivatives are obtained [Bibliography, e.g., Verardo et al. Synthesis (1993), 121; Synthesis (1991), 447; Kawaguchi, Synthesis (1985), 701; Micovic et al. Synthesis (1991), 1043].

The acylation of an amino group is carried out in the usual way, for example, with an acid halide or acid anhydride optionally in the presence of a base such as dimethylaminopyridine in solvents such as methylene chloride, tetrahydrofuran or pyridine, according to the Schotten-Baumann variant in aqueous solution at weakly alkaline pH or by reaction with an anhydride in glacial acetic acid.

The introduction of the halogens chlorine, bromine or iodine via the amino group can be carried out, for example, also according to Sandmeyer, by the diazonium salts that are intermediately formed with nitrites being reacted with copper(I) chloride or copper(I) bromide in the presence of the corresponding acid such as hydrochloric acid or hydrobromic acid or with potassium iodide. If an organic nitrite is used, the halogen can be introduced in a solvent such as, for example, dimethylformamide, e.g., by addition of methylene iodide or tetrabromomethane.

The introduction of fluorine is possible, for example, by Balz Schiemann reaction of diazonium tetrafluoroborate.

The isomer mixtures can be separated into enantiomers or E/Z-isomers according to commonly used methods, such as, for example, crystallization, chromatography or salt formation.

The production of salts is carried out in the usual way by a solution of the compound of formula I being mixed with the equivalent amount of acid or excess acid, which optionally is in solution, and the precipitate being separated or the solution being worked up in the usual way.

In so far as the production of the starting compounds is not described, the latter are known, or it is carried out analogously to known compounds (e.g., DE 3527117, Patent 879404, EP 0492485, HU 191702, FR 2566774, HU 194550, HU 194529, BP 2034706).

The following examples explain the production of the compounds according to the invention.

EXAMPLE 1

7-Acetyl-5-(4-nitrophenyl)-8-methyl-7H-1,3-dioxolor[4,5-h][2,3]-benzodiazepine

A suspension of 1.0 g (3.1 mmol) of 5-(4-nitrophenyl)-8-methyl-9H-7H-1,3-dioxolo[4,5-h][2,3]-benzodiazepine is heated in 10 ml of acetic anhydride for 7 hours to 130°–140° C. The solution is poured on ice, and the precipitate is suctioned off. 0.99 g (87% of theory) of a yellow powder is obtained. After combining the corresponding fractions and concentration by evaporation, flash chromatography of this crude product on silica gel 60 with benzene/ethyl acetate (4:1) as a mobile solvent yields 0.78 g (70% of theory) of 7-acetyl-5-(4-nitrophenyl)-8-methyl-7H-1,3-dioxolo[4,5-h][2,3]-benzodiazepine as a solid with a melting point of 200°–202° C. A sample is recrystallized from ethanol and then has a melting point of 205°–207° C. (minor decomposition).

Similarly produced is:
7-Acetyl-5-(4-N-acetylaminophenyl)-8-methyl-7H-1,3-dioxolo[4,5-h][2,3]-benzodiazepine

EXAMPLE 2

7-Acetyl-5-(4-aminophenyl)-8-methyl-7H-1,3-dioxolor[4,5-h][2,3]-benzodiazeipine 0.1 g of Raney nickel and 0.25 ml (4.93 mmol) of 98% hydrazine hydrate are added to a suspension of 0.6 g (1.64 mmol) of 7-acetyl-5-(4-nitrophenyl)-8-methyl-7H-1,3-dioxolo[4,5-h][2,3]-benzodiazepine in 40 ml of methanol. The mixture is stirred for 0.5 hour. The starting material is dissolved within a few minutes. After the reaction is completed, catalyst is filtered out. The filtrate is concentrated by evaporation in a vacuum. The residue is absorptively precipitated in water, suctioned off and rewashed with water. 0.49 g of 7-acetyl-5-(4-aminophenyl)-8-methyl-7H-1,3-dioxolo[4,5-h][2,3]-benzodiazepine with a melting point of 175°–180° C. is obtained. Recrystallization of this crude product from 50% aqueous ethanol yields 0.46 g (79%) of 7-acetyl-5-(4-amino-phenyl)-8-methyl-7H-1,3-dioxolo[4,5-h][2,3]-benzodiazepine with a melting point of 208°–210° C.

$^1$H-NMR (CDCl$_3$): d: 2.23 (s, 3H), 2.26 (br s, 3H), 4.02 (br s, 2H), 5.97 (br s, 1H), 6.05 (br s, 1H), 6.32 (br s, 1H), 6.64 (d, 2H), 6.74 (s, 2H), 7.33 (d, 2H):

Elementary analysis: Calculated for $C_{19}H_{17}N_3O_3 \cdot H_2O$ (353.36): C=64.68%; H=5.42%; N=11.89%; Fnd: C=64.74%; H=4.89%; N=11.92%;

EXAMPLES 3–18

Analogously to Example 1, the compounds of formula I that are described in Table 1 and in which $R^5$, $R^6$ and $R^7$ mean hydrogen, n=1 and $R^4$=methyl are obtained

TABLE 1

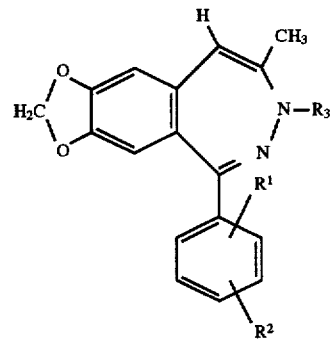

| Example No. | $R^1$ | $R^2$ | $R^3$ | Melting point, °C. |
|---|---|---|---|---|
| 3 | 4-NO$_2$ | H | propionyl | 206–208 |
| 4 | 3-NO$_2$ | H | acetyl | 198–200 |
| 5 | 2-NO$_2$ | H | acetyl | 192–194 |
| 6 | 4-NO$_2$ | H | pivaloyl | 225–227 |
| 7 | 4-NO$_2$ | H | trifluoro-acetyl | 213–215 |

TABLE 1-continued

| Example No. | $R^1$ | $R^2$ | $R^3$ | Melting point, °C. |
|---|---|---|---|---|
| 8 | 2-Cl | H | acetyl | 197–198 |
| 9 | 2-CH$_3$ | H | acetyl | 182–184 |
| 10 | 4-OCH$_3$ | H | acetyl | 173–176 |
| 11 | 3-OCH$_3$ | H | acetyl | 120–122 |
| 12 | 3-Cl | H | acetyl | 130–132 |
| 13 | 4-F | H | acetyl | 208–210 |
| 14 | 4-NO$_2$ | 2-Br | acetyl | oil |
| 15 | 4-OCH$_3$ | 2-ipropyl | acetyl | 96–98 |
| 16 | 4-OCH$_3$ | 3-F | acetyl | 196–198 |
| 17 | 3-CF$_3$ | H | acetyl | 210–212 |
| 18 | 4-CF$_3$ | H | acetyl | 122–124 |

EXAMPLE 19

7-Cyclopropanecarbonyl-8-methyl-5-phenyl-7H-1,3-dioxolor4,5-enzodiazepine

A suspension of 0.56 g (2.0 mmol) of 8-methyl-5-phenyl-9-H-1,3-dioxolo[4,5-h][2,3]-benzodiazepine and 0.41 g (3.0 mmol) of potassium carbonate in 15 ml of benzene are heated to boiling, and 0.31 g (3.0 mmol) of cyclopropanecarbonyl chloride is added. At this temperature, it is stirred for 1.5 more hours and then filtered. After the solvent is removed, the residue is chromatographed on silica gel 60 with hexane/ethyl acetate 2:1 as eluant. After crystallization of the main fraction from ethanol, 0.35 g (50%) of the title compound with a melting point of 165°–166° C. is obtained.

EXAMPLES 20–26

Analogously to Example 19, the compounds of formula 1 that are described in Table 2 and in which $R^5$, $R^6$ and $R^7$ mean hydrogen, n=1 and $R^4$=methyl are obtained

TABLE 2

| Example No. | $R^1$ | $R^2$ | $R^3$ | Melting point, °C. |
|---|---|---|---|---|
| 20 | 4-NO$_2$ | H | benzoyl | >212° C. |
| 21 | 4-NO$_2$ | H | 3-chloro- | 260–263° C. |

TABLE 2-continued

| Example No. | $R^1$ | $R^2$ | $R^3$ | Melting point, °C. |
|---|---|---|---|---|
| 20 | 4-NO$_2$ | H | benzoyl | >212° C. |
|    |          |   | benzoyl |          |
| 22 | 4-NO$_2$ | H | cyclopropanecarbonyl | further processed |
| 23 | 4-NO$_2$ | H | methacryloyl | further processed |
| 24 | 4-NO$_2$ | H | isobutyryl | further processed |
| 25 | 4-NO$_2$ | H | isovaleryl | further processed |
| 26 | 4-NO$_2$ | H | butyryl | further processed |

EXAMPLE 27

7-Formyl-5-(4-nitrophenyl)-8-methyl-7H-1,3-dioxolo [4,5-h][2,3]benzodiazepine

Analogously to Example 1, the title compound is obtained with a mixture of acetic anhydride and 98% formic acid 3:1. After chromatography on silica gel with benzene/ethyl acetate 4:1 as eluant, brown crystals are obtained, melting point 123°–127° C. (36%).

EXAMPLE 28

7-Ethoxycarbonyl-5-(4-nitrophenyl)-8-methyl-7H-1,3-dioxolo[4,5][2,3]benzodiazepine 5-(4-Nitrophenyl)-8-methyl-9H-1,3-dioxolo[4,5-h][2,3]-benzodiazepine (0.323 g/1.0 mmol), anhydrous potassium carbonate (0.28 g, 2.0 mmol), ethyl chloroformate (0.12 ml, 1.2 mmol) and anhydrous benzene are refluxed while being stirred. In each case after 1 hour and after 12 hours, ethyl chloroformate (0.12 ml) and potassium carbonate (0.28 g) are added. After 18 hours, it is filtered off, concentrated, and the residue is chromatographed on silica gel with benzene-:ethyl acetate as eluant. 92 mg of yellow amorphous crystals (23%), which are further processed without purification, are obtained.

EXAMPLE 29

8-Methyl-7-methylcarbamoyl-5-(4-nitrophenyl)-7H-1,3-dioxolo [4,5-h][2,3]benzodiazepine A: A mixture of 5-(4-nitrophenyl)-8-methyl-9H-1,3-dioxolo[4,5-h][2,3]benzodiazepine (1.61 g, 5.0 mmol), phenyl chloroformate (1.5 ml, 12.0 mmol), potassium carbonate (1.4 g, 10 mmol) and benzene (50 ml) are refluxed for 1.5 hours while being stirred. The reaction mixture is hot-filtered, concentrated by evaporation, and the residue is absorptively precipitated with 15 ml of ethyl acetate. The filtrate is concentrated by evaporation and used in the next reaction step without further purification.

B: The residue that is obtained according to A is mixed with 10 ml of DMF and 3 ml of a 40% solution of methylamine in water, heated to 100° C. and after 16 hours added to water. After extraction with chloroform, it is worked up in the usual way, and 0.307 g of the title compound (16%) is obtained.

EXAMPLE 30

8-Methyl-7-methoxycarbonyl-5-(4-nitrophenyl)-7H-1,3-dioxolo [4,5-h][2,3]benzodiazepine 1.85 g (3.9 mmol) of the product obtained after Example 29, reaction step A is mixed with 90 ml of anhydrous methanol and 15 ml of a 50% solution of methylamine in methanol. A catalytic amount of NaCN is added, and it is heated for 18 hours to 90° C. It is worked up in the usual way. After chromatography with benzene/ethyl acetate 2:1, 0.44 g (30%) of the title compound is obtained.

EXAMPLES 31–47

Analogously to Example 2, the compounds of formula I that are described in Table 3 and in which $R^4$ methyl, n=1, and $R^5$, $R^6$ and $R^7$ mean hydrogen are obtained

TABLE 3

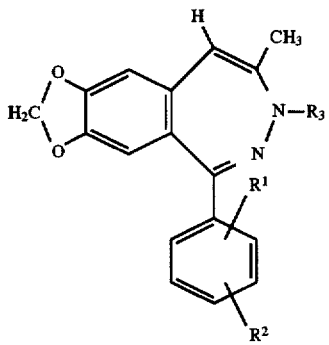

| Example No. | $R^1$ | $R^2$ | $R^3$ | Melting point, °C. |
|---|---|---|---|---|
| 31 | 4-NH₂ | H | formyl | with ½ eq. H₂O, 141–145 without water 186 |
| 32 | 4-NH₂ | H | propionyl | without water: 186, 170–172 |
| 33 | 3-NH₂ | H | acetyl | 196–198 |
| 34 | 4-NH₂ | H | benzoyl | 206–207 |
| 35 | 4-NH₂ | H | 3-chlorobenzoyl | 132–134 |
| 36 | 4-NH₂ | H | cyclopropanecarbonyl | 215–217 |
| 37 | 4-NH₂ | H | methacryloyl | 127–132 |
| 38 | 4-NH₂ | H | isobutyryl | 130–135 |
| 39 | 4-NH₂ | H | isovaleryl | 100–103 |
| 40 | 4-NH₂ | H | butyryl | 114–116 |
| 41 | 4-NH₂ | H | pivaloyl | 206–208 |
| 42 | 4-NH₂ | H | trifluoroacetyl | 142–145 |
| 43 | 2-NH₂ | H | acetyl | 157–158 |
| 44 | 4-NH₂ | 2-Br | acetyl | 250–252 |
| 45 | 4-NH₂ | H | methylcarbamoyl | 157–167 |
| 46 | 4-NH₂ | H | ethoxycarbonyl | 142–144 |
| 47 | 4-NH₂ | H | methoxycarbonyl | 144–148 |

EXAMPLE 48

7-Acetyl-5-(4-nitrophenyl)-8-ethyl-7H-1,3-dioxolo [4,5-h][2,3]benzodiazepine

A: 7-Ethyl-5-(4-nitrophenyl)-1,3-dioxolo[4,5-g] isochroman 1-(3-Benzodioxol-5-yl)-butan-2-one (Nichols et al., J. Med. Chem. 1986, 29, 2009) is reduced to the corresponding isobutanol, and the latter is reacted with 4-nitrobenzaldehyde according to Hungarian Patent HU 194550 (C.A. 105, 1986, 226357V) to the title compound. Yield 85%, melting point 116°–118° C. (methanol).

B: 7-Ethyl-5-(4-nitrophenyl)-1,3-dioxolo [4,5-g][2] benzopyrylium perchlorate

The isochroman compound that is obtained according to reaction step A is oxidized according to Hungarian Patent HU 194529 (C.A. 105, 1986, 152712h) to the corresponding diketone, which is transferred with 70% HClO₄ into the benzopyrylium salt. Yield 50%, melting point 243°–245° C. (decomposition)

C: 8-Ethyl-5-(4-nitrophenyl)-9H-1,3-dioxolo [(4,5-h][2, 3]benzodiazepine

The pyrylium salt that is obtained according to B is reacted with hydrazine hydrate according to British Patent BP 20 34 706 (C.A. 94, 1981, 103443S) to 9-H-2,3-benzodiazepine. Yield 88%, melting point 218°–220° C. (DMF).

D: The product that is obtained according to reaction step C is acetylated analogously to Example 1. The title compound is obtained with melting point 132°–134° C. (ethanol), yield 33%.

EXAMPLE 49

7-Acetyl-5-(4-aminophenyl)-8-ethyl-7H-1,3-dioxolo [4,5-h][2,3]benzodiazepine

The compound that is obtained according to Example 48 is reduced analogously to Example 2. Yield 45%, melting point 136°–138° C. (ethanol/water 1:1).

EXAMPLE 50

8-Acetyl-9-methyl-6-(4-nitrophenyl)-8H-2,3-dihydro-1,4-dioxanor[2,3-h][2,3benzodiazepine A: 6,7-Dihydroxy-3-methyl-1-(4-nitrophenyl)-2-benzopyrylium-perchlorate 44.0 g of 3-methyl-6,7-dimethoxy-1-(4-nitrophenyl)-2-benzopyrylium-perchlorate (C.A. 105, 1986, 152712h) is added to a solution of 46.3 g of AlCl₃ in 170 ml of nitromethane and heated to boiling for 4 hours. The solvent is removed, the residue is treated with 500 ml of cooled 50% HCl solution, and the product that is obtained is washed with cold water. 43.5 g of crude product, which is mixed with 130 ml of acetic acid, heated to boiling and mixed with 13.3 ml of 70% HClO₄, is obtained. After cooling, 30.0 g of the title compound (73%) with melting point 253°–255° C. (decomposition ethyl acetate) is obtained.

B: 7,8-Dihydroxy-4-methyl-1-(4-nitrophenyl)-5H-2,3-benzodiazepine

The compound of reaction step A is reacted with hydrazine hydrate analogously to C.A. 94, 1981, 1034435 to the title compound, melting point 254°–256° C. (decomposition).

C: 9-Methyl-6-(4-nitrophenyl)-10H-2,3-dihydro-1,4-dioxano [2,3-h][2,3]benzodiazepine 4.8 g of KF and 1.12 ml of 1,2-dibromoethane are added to a suspension of 3.0 g of the compound that is obtained according to reaction step B in 37 ml of dry DMF, and the mixture is stirred for 1 hour at 110°–120° C. After cooling, the reaction mixture is added to 250 ml of water, the product is filtered off, washed with water and worked up in the usual way. 1.42 g (44%) of the title compound with melting point 228°–230° C. (decomposition) is obtained.

D: The compound that is obtained according to C is acetylated analogously to Example 1, yield 82%, melting point 226°–228° C. (decomposition).

EXAMPLE 51

8-Acetyl-9-methyl-6-(4-aminophenyl)-8H-2,3-dihydro-1,4-dioxanor2,3-h][2,3]benzodiazepine The compound that is obtained according to Example 50 is reduced analogously to Example 2. Yield 72%, melting point 231°–233° C. (decomposition).

EXAMPLE 52

9-Acetyl-10-methyl-7-(4-nitrophenyl)-2,3,4,9-tetrahydro-1,5-dioxepino-[2,3-h][2,3]benzodiazepine

A: 10-Methyl-7-(4-nitrophenyl)-2,3,4,11-tetrahydro-1,5-dioxepino[2,3-h][2,3]benzodiazepine The process that is described in reaction step C of Example 50 is performed with 1,3-dibromopropane, and the title compound is obtained in 40% yield with melting point 204°–206° C. (DMF/water 10:1).

B: The acetylation is carried out analogously to Example 1, and the title compound is obtained in 65% yield with the melting point of 202°–204° C.

EXAMPLE 53

9-Acetyl-10-methyl-7-(4-aminophenyl)-2,3,4,9-tetrahydro-1,5-dioxepinor[2,3-h][2,3]benzodiazepine

The compound that is obtained according to Example 52 is reduced analogously to Example 2, and the title compound is obtained in 66% yield with the melting point of 183°–184° C.

We claim:

1. Compounds of formula I,

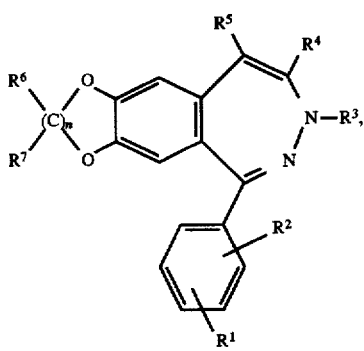

in which $R^1$ and $R^2$ are the same or different and mean hydrogen, $C_1$–$C_6$ alkyl, nitro, halogen, the group —$NR^8R^9$, —O—$C_{1-4}$ alkyl or —$CF_3$, $R^3$ means the group

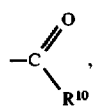

$R^4$ means optionally substituted $C_1$–$C_6$ alkyl, $R^5$ means hydrogen or optionally substituted $C_1$–$C_6$ alkyl, $R^6$ and $R^7$ are the same or different and mean hydrogen, optionally substituted $C_1$–$C_6$ alkyl or optionally substituted aryl, $R^8$ and $R^9$ are the same or different and mean hydrogen, $C_1$–$C_6$ alkyl or the group

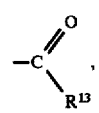

$R^{10}$ means hydrogen, optionally substituted $C_1$–$C_6$ alkyl, optionally substituted aryl, the group —$NR^{11}R^{12}$, —O—$C_{1-6}$ alkyl, $C_{3-7}$ cycloalkyl, $C_{2-6}$ alkenyl or —O—$C_{3-7}$ cycloalkyl, $R^{11}$ and $R^{12}$ are the same or different and mean hydrogen, optionally substituted $C_1$–$C_6$ alkyl or optionally substituted aryl, and $R^{13}$ means $C_1$–$C_6$ alkyl and n stands for 1, 2 or 3 as well as their physiologically compatible salts and isomers.

2. Compounds of formula 1, according to claim 1, in which $R^1$ means nitro or amino, $R^2$ means hydrogen, $C_1$–$C_6$ alkyl, nitro, halogen, the group —$NR^8R^9$, —O—$C_{1-4}$ alkyl or —$CF_3$, $R^3$ means the group

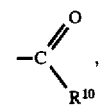

$R^4$ means optionally substituted $C_1$–$C_6$ alkyl, $R^5$ means hydrogen or optionally substituted $C_1$–$C_6$ alkyl, $R^6$ and $R^7$ are the same or different and mean hydrogen, optionally substituted $C_1$–$C_6$ alkyl or optionally substituted aryl, $R^8$ and $R^9$ are the same or different and mean hydrogen, $C_1$–$C_6$ alkyl or the group

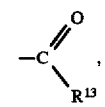

$R^{10}$ means hydrogen, optionally substituted $C_1$–$C_6$ alkyl, optionally substituted aryl, the group —$NR^{11}R^{12}$, —O—$C_{1-6}$ alkyl, $C_{3-7}$ cycloalkyl, $C_{2-6}$ alkenyl or —O—$C_{3-7}$ cycloalkyl, $R^{11}$ and $R^{12}$ are the same or different and mean hydrogen, optionally substituted $C_1$–$C_6$ alkyl or optionally substituted aryl, $R^{13}$ means $C_1$–$C_6$ alkyl and n stands for 1, 2 or 3 as well as their physiologically compatible salts and isomers.

3. Compounds of formula 1, according to claim 1, in which $R^1$ means nitro or amino, $R^2$ means hydrogen, $C_1$–$C_6$ alkyl, nitro, halogen, the group —$NR^8R^9$, —O—$C_{1-4}$ alkyl or —$CF_3$, $R^3$ means the group

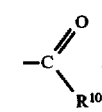

$R^4$ means $C_1$–$C_6$ alkyl optionally substituted by $C_1$–$C_6$ alkoxy, halogen or $C_1$–$C_6$ alkanoyl, $R^5$ means hydrogen or $C_1$–$C_6$ alkyl optionally substituted by $C_1$–$C_6$ alkoxy, halogen or $C_1$–$C_6$ alkanoyl, $R^6$ and $R^7$ are the same or different and mean hydrogen, $C_1$–$C_6$ alkyl optionally substituted by $C_1$–$C_6$ alkoxy, halogen or $C_1$–$C_6$ alkanoyl, or aryl, $R^8$ and $R^9$ are the same or different and mean hydrogen, $C_1$–$C_6$ alkyl or the group

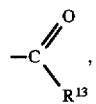

R¹⁰ means hydrogen, optionally substituted $C_1$–$C_6$ alkyl, optionally substituted aryl, the group —$NR^{11}R^{12}$, —O—$C_{1-6}$ alkyl, $C_{3-7}$ cycloalkyl, $C_{2-6}$ alkenyl or —O—$C_{3-7}$ cycloalkyl, $R^{11}$ and $R^{12}$ are the same or different and mean hydrogen, $C_{1-C6}$ alkyl optionally substituted by $C_{1-C6}$ alkoxy, halogen or $C_1$–$C_6$ alkanoyl, or aryl, $R^{13}$ means $C_1$–$C_6$ alkyl and n stands for 1, 2 or 3 as well as their physiologically compatible salts and isomers.

4. Compounds of general formula 1, according to claim 1, in which $R^1$ means nitro or amino, $R^2$ means hydrogen, $R^3$ means the group

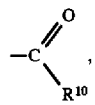

$R^4$ means methyl or ethyl, $R^5$, $R^6$ and $R^7$ mean hydrogen, $R^{10}$ means hydrogen, $C_1$–$C_6$ alkyl, phenyl optionally substituted with halogen, the group —$NR^{11}R^{12}$, $C_{3-7}$ cycloalkyl, $C_{2-6}$ alkenyl, —O—$C_{1-6}$ alkyl or $C_{1-6}$ alkyl which is substituted in one or more places with fluorine, $R^{11}$ and $R^{12}$ are the same or different and mean hydrogen, $C_1$–$C_4$ alkyl or phenyl, and n is 1, 2 or 3, as well as their physiologically compatible salts and isomers.

5. Process for the production of compounds of general formula I, wherein a compound of general formula II

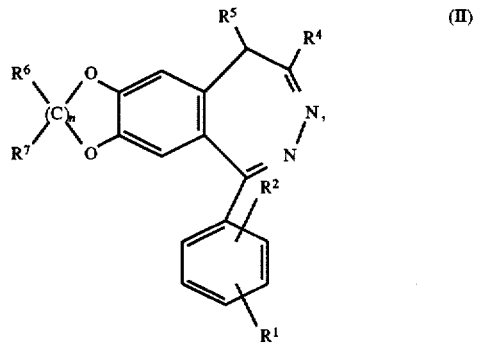

in which $R^1$, $R^2$, $R^4$, $R^5$, $R^7$ and n have the meanings indicated in general formula I is acylated, and optionally the nitro group is catalytically reduced at $R^1$ and/or $R^2$ and then the carbamoyl group is optionally acylated, allkylated, or halogenated with organic amines or the ester group is reacted with an alcohol, and/or the isomers are separated or the salts are formed.

6. Phamaceutical agent that contains a compound of general formula I according to claim 1 and a pharmaceutically acceptable carrier.

7. A method of treating a neurological or psychiatric disorder mediated by overstimulation of the AMPA receptor comprising administering a compound according to claim 1.

8. A method of treating amyotrophic lateral sclerosis comprising administering a compound of claim 1 to a patient in need of such treatment.

* * * * *